US007112408B2

(12) United States Patent  
Ye et al.

(10) Patent No.: US 7,112,408 B2  
(45) Date of Patent: Sep. 26, 2006

(54) DETECTION OF OVARIAN CANCER BASED UPON ALPHA-HAPTOGLOBIN LEVELS

(75) Inventors: Bin Ye, Brookline, MA (US); Samuel C. Mok, Brookline, MA (US); Daniel W. Cramer, Chestnut Hill, MA (US); Ross S. Berkowitz, Waban, MA (US); Steven Skates, Cambridge, MA (US)

(73) Assignee: The Brigham and Women's Hospital, Inc., Boston, MA (US)

(*) Notice: Subject to any disclaimer, the term of this patent is extended or adjusted under 35 U.S.C. 154(b) by 460 days.

(21) Appl. No.: 10/162,221

(22) Filed: Jun. 5, 2002

(65) Prior Publication Data

US 2003/0017515 A1 Jan. 23, 2003

Related U.S. Application Data

(60) Provisional application No. 60/296,458, filed on Jun. 8, 2001.

(51) Int. Cl.  
*G01N 33/53* (2006.01)

(52) U.S. Cl. ............. 435/7.1; 435/7.23; 435/7.9; 435/7.91; 435/7.92; 530/387.1

(58) Field of Classification Search ............ 435/7.1, 435/7.23, 7.91, 7.92, 7.93, 7.94, 7.95, 7.9; 530/387.1; 424/184.1, 185.1  
See application file for complete search history.

(56) References Cited

U.S. PATENT DOCUMENTS

| | | | |
|---|---|---|---|
| 5,604,106 A | 2/1997 | Liotta et al. | 435/7.23 |
| 5,695,761 A | 12/1997 | Denhardt et al. | 424/184.1 |
| 5,712,104 A | 1/1998 | Yamamoto | 435/7.92 |
| 5,801,004 A | 9/1998 | Hudson et al. | 435/7.23 |
| 5,866,119 A | 2/1999 | Bandman et al. | 424/94.6 |
| 5,928,883 A | 7/1999 | Gleich et al. | 435/7.21 |
| 6,414,219 B1 | 7/2002 | Denhardt et al. | 800/18 |
| 6,686,444 B1 | 2/2004 | Ashkar | 530/329 |
| 2002/0039753 A1 | 4/2002 | Chai et al. | 435/7.23 |
| 2002/0052308 A1 | 5/2002 | Rosen et al. | 514/1 |

OTHER PUBLICATIONS

Kibel, AS et al, 2000, J urol, 164(1): 192-6.*  
Zhau, HE, 1994, J Cell Biochem, Suppl 19: 208-216.*  
Cheung S T et al, 2002, Cancer Research, 62(16): 4711-21.*  
Ren, C et al, 1998, Cancer Res, 58(6): 1285-90.*  
Gingrich, JR et al, 1996, Cancer res, 56(18): 4096-4102.*  
Ko, TM, Chinese J Microbiol. Immunol.:149-1 57 (1980).*  
Ali, et al., "Intercellular Cell Adhesion Molecule-1, Vascular Cell Adhesion Molecule-1, and Regulated on Activation Normal T Cell Expressed and Secreted Are Expressed by Human Breast Carcinoma Cells and Support Eosinophil and Activation," *Am. J. Path.* 157:313-321 (2000).  
Alper, "Turning Sweet on Cancer," *Science* 301:159-160 (2003).

Barker, et al., "Eosinophil Cationis Protein cDNA, Comparison with Other Toxic Cationic Proteins and Ribonucleases," *J. Immunol.* 143:952-955 (1989).  
Beintema, et al., "Amino Acid Sequence of the Nonsecretory Ribonuclease of Human Urine," *Biochemistry* 27:4530-4538 (1988).  
Berteau, et al., "Prostasin mRNA to Detect Prostate Cells in Blood of Cancer Patients," *Clin. Chem. Lab. Med.* 37:S119 (1999).  
Blumenthal, et al., "Degranulating Eosinophils in Human Endometriosis," *Am. J. Path.* 156:1581-1588 (2000).  
Chen, et al., "Down-Regulation of Prostasin Serine Protease: A Potential Invasion Suppressor in Prostate Cancer," *Prostate* 48:93-103 (2001).  
Chen, et al., "Prostasin Serine Protease Inhibits Breast Cancer Invasiveness and Is Transcriptionally Regulated by Promoter DNA Methylation," *Int. J. Cancer* 97:323-329 (2002).  
Coolen, et al., "Elevation of Brain-Type Creatine Kinase in Serum from Patients with Carcinoma," *Cancer* 44:1414-1418 (1979).  
Denhardt, et al., "Osteopontin: A Protein with Diverse Functions," *FASEB J.* 7:1475-1482 (1993).  
DeRisi, et al., "Use of a cDNA Microarray to Analyse Gene Expression Patterns in Human Cancer," *Nature Genetics* 14:457-460 (1996).  
Dorta, et al., "Tumour-Associated Tissue Eosinophilia as a Prognostic Factor in Oral Squamous Cell Carcinomas," *Histopathology* 41:152-157 (2002).  
Fernández-Aceñero, et al., "Prognostic Influence of Tumor-Associated Eosinophilic Infiltrate in Colorectal Carcinoma," *Cancer* 88:1544-1548 (2000).  
Giachelli, et al., "Molecular and Cellular Biology of Osteopontin," *Trends Cardiovasc. Med.* 5:88-95 (1995).  
Hakomori, "Glycosylation Defining Cancer Malignancy: New Wine in an Old Bottle," *Proc. Natl. Acad. Sci. USA* 99:10231-10233 (2002).  
Hamann, et al., "Sequence of Human Eosinophil-Derived Neurotoxin cDNA: Identity of Deduced Amino Acid Sequence with Human Nonsecretory Ribonucleases," *Gene* 83:161-167 (1989).  
Hamann, et al., "Structure and Chromosome Localization of the Human Eosinophil-Derived Neurotoxin and Eosinophil Cationic Protein Genes: Evidence for Intronless Coding Sequences in the Ribonuclease Gene Superfamily," *Genomics* 7:535-546 (1990).  
Heid, et al., "Real Time Quantitative PCR," *Genome Res.* 6:986-994 (1996).  
Hooper, et al., "Testisin, a New Human Serine Proteinase Expressed by Premeiotic Testicular Germ Cells and Lost in Testicular Germ Cell Tumors," *Cancer Res.* 59:3199-3205 (1999).  
Hooper, et al., "Localization, Expression and Genomic Structure of the Gene Encoding the Human Serine Protease Testisin," *Biochimica et Biophysica Acta* 1492:63-71 (2000).

(Continued)

*Primary Examiner*—Jeffrey Siew  
*Assistant Examiner*—Minh-Tam Davis  
(74) *Attorney, Agent, or Firm*—Fitch, Even, Tabin, & Flannery

(57) ABSTRACT

The present invention is directed to a method for determining whether a woman has, or is likely to develop, ovarian cancer based upon assays of the alpha subunit of haptoglobin.

18 Claims, No Drawings

OTHER PUBLICATIONS

Kakugawa, et al., "Up-Regulation of Plasma Membrane-Associated Ganglioside Sialidase (Neu3) in Human Colon Cancer and Its Involvement in Apoptosis Suppression," *Proc. Natl. Acad. Sci. USA* 99:10718-10723 (2002).

Kiefer, et al., "The cDNA and Derived Amino Acid Sequence for Human Osteopontin," *Nuc. Ac. Res.* 17:3306 (1989).

Kodama, et al., "Large Cell Carcinoma of the Lung Associated with Marked Eosinophilia," *Cancer* 54:2313-2317 (1984).

Kurtz, et al., "Serum Creatine Kinase BB Isoenzyme as a Diagnostic Aid in Occult Small Cell Lung Cancer," *Cancer* 56:562-566 (1985).

Mok, et al., "Molecular Cloning of Differentially Expressed Genes in Human Epithelial Ovarian Cancer," *Gynecologic Oncol.* 52:247-252 (1994).

Mok, et al., "SPARC, an Extracellular Matrix Protein with Tumor-Suppressing Activity in Human Ovarian Epithelial Cells," *Oncogene* 12:1895-1901 (1996).

Müeller-Pillasch, et al., "Cloning of a Gene Highly Overexpressed in Cancer Coding for a Novel KH-Domain Containing Protein," *Oncogene* 14:2729-2733 (1997).

Oldberg, et al., "Cloning and Sequence Analysis of Rat Bone Sialoprotein (Osteopontin) cDNA Reveals an Arg-Gly-Asp Cell-Binding Sequence," *Proc. Natl. Acad. Sci. USA* 83:8819-8823 (1986).

Oldberg, et al., "Identification of a Bone Sialoprotein Receptor in Osteosarcoma Cells," *J. Biol. Chem.* 263:19433-19436 (1988).

Pastrňák, et al., "Local Eosinophilia in Stroma of Tumors Related to Prognosis," *Neoplasma* 31:323-326 (1984).

Patarca, et al., "Differential Induction of Interferon γ Gene Expression after Activation of CD4+ Cells by Conventional Antigen and Mls Superantigen," *Proc. Natl. Acad. Sci. USA* 882736-2739 (1991).

Rosenberg, et al., "Molecular Cloning of the Human Eosinophil-Derived Neurotoxin: A Member of the Ribonuclease Gene Family," *Proc. Natl. Acad. Sci. USA* 86:4460-4464 (1989).

Sakakibara, et al., "A Putative Mouse Oocyte Maturation Inhibitory Protein from Urine of Pregnant Women: N-Terminal Sequence Homology with Human Nonsecretory Ribonuclease," *Chem. Pharm. Bull.* 39:146-149 (1991).

Sakakibara, et al., "Characterization of a Unique Nonsecretory Ribonuclease from Urine of Pregnant Women," *J. Biochem.* 111:325-330 (1992).

Samoszuk, et al., "New Marker for Blood Vessels in Human Ovarian and Endometrial Cancers," *Clin. Cancer Res.* 2:1867-1871 (1996).

Samoszuk, et al., "Occult Deposition of Eosinophil Peroxidase in a Subset of Human Breast Carcinomas," *Am. J. Pathol.* 148:701-706 (1996).

Samoszuk, "Eosinohils and Human Cancer," *Histol. Histopathol.* 12:807-812 (1997).

Schleich, et al., "Serum Ribonuclease Activity in Patients with Ovarian Tumors," *Eur. J. Gynaec. Oncol.* 7:76-81 (1986).

Schleich, et al., "Ovarian Carcinoma: Increase in Clinical Validity by Simultaneous Determination o f SRA and CA 125," *J. Cancer Res. Clin. Oncol.* 113:603-607 (1987).

Schneider, et al., "Osteopontin But Not Osteonectin Messenger RNA Expression Is a Prognostic Marker in Curatively Resected Non-Small Cell Lung Cancer," *Clin. Cancer Res.* 10:1588-1596 (2004).

Schriml, et al., "Tyramide Signal Amplification (TSA)-FISH Applied to Mapping PCR-Labeled Probes Less Than 1 kb in Size," *BioTechniques* 27:608-613 (1999).

Schummer, et al., "Comparative Hybridization of an Array of 21 500 Ovarian cDNAs for the Discovery of Genes Overexpressed in Ovarian Carcinomas," *Gene* 238:375-385 (1999).

Schwartz, "The Hypereosinophilic Syndrome and the Biology of Cancer," *N. Engl. J. Med.* 348:1199-1200 (2003).

Senger, et al., "Elevated Expression of Secreted Phosphoprotein 1 (Osteopontin, 2ar) as a Consequence of Neoplastic Transformation," *Anticancer Res.* 9:1291-1300 (1989).

Sharp, et al., "Tumor Cells Are the Source of Osteopontin and Bone Sialoprotein Expression in Human Breast Cancer," *Lab. Investig.* 79:869-877 (1999).

Sheid, et al., "Plasma Rinonuclease, A Marker for the Detection of Ovarian Cancer," *Cancer* 39:2204-2208 (1977).

Smith, et al., "Molecular Cloning of a Tumor Promoter-Inducible mRNA Found in JB6 Mouse Epidermal Cells: Induction Is Stable at High, but Not at Low, Cell Densities," *J. Cell. Biochem.* 34:13-22 (1987).

Suster, "Tumors of the Skin Composed of Large Cells with Abundant Eosinophilic Cytoplasm," *Semin. Diagn. Pathol.* 16:162-177 (1999).

Szala, et al., "Molecular Cloning of cDNA for the Carcinoma-Associated Antigen GA733-2," *Proc. Natl. Acad. Sci. USA* 87:3542-3546 (1990).

Tuck, et al., "Osteopontin Induces Increased Invasiveness and Plasminogen Activator Expression of Human Mammary Epithelial Cells," *Oncogene* 18:4237-4246 (1999).

Wang et al., "Monitoring Gene Expression Profile Changes in Ovarian Cancer Carcinomas Using cDNA Microarray," *Gene* 229:101-108 (1999).

Ye, et al., "Identification and Validation of Urinary Biomarkers for Early Stage of Ovarian Cancer by Multiple Proteomic Approaches," *Proc. Am. Assoc. Cancer Res.* 45:915 (abstract 3964 (2004)).

Ye, et al., "Haptoglobin-α Subunit as Potential Serum Biomarker in Ovarian Cancer: Identification and Characterization Using Proteomic Profiling and Mass Spectrometry," *Clin. Cancer Res.* 92904-2911 (2003).

Yiu, et al., "Prostasin, a Potential Serum Marker for the Early Detection of Ovarian Cancer," *Proceedings of the American Association for Cancer Research Annual* 42:744 (2001).

Yu, et al., "Prostasin Is a Novel Human Serine Proteinase from Serminal Fluid," *J. Biol. Chem.* 269:18843-18848 (1994).

Yu, et al., "Molecular Cloning, Tissue-Specific Expression, and Cellular Localization of Human Prostasin mRNA," *J. Biol. Chem.* 270:13483-13489 (1995).

Bast, et al., "A Radioimmunoassay Using a Monoclonal Antibody to Monitor the Course of Epithelial Ovarian Cancer," *N. Engl. J. Med.* 309:883-887 (1983).

Cramer, et al., "Carotenoids, Antioxidants and Ovarian Cancer Risk in Pre- and Postmenopausal Women," *Int. J. Cancer* 94:128-134 (2001).

Daly, et al., "The Search for Predictive Patterns in Ovarian Cancer: Proteomics Meets Bioinformatics," *Cancer Cell* 1:111-112 (2002).

Fish, et al., "Serum Haptoglobin and α1-Acid Glycoprotein as Indicators of the Effectiveness of cis- Diamminedichloroplatinum (CDDP) in Ovarian Cancer Patients—a Preliminary Report," *Eur. J. Cancer Clin. Oncol.* 20:625-630 (1984).

Harvey, et al., "Cancer Cells Release a Covalent Complex Containing Disulfide-Linked Domains from Urinary Plasminogen Activator, Neural Cell Adhesion Molecule, and Haptoglobin α and β Chains," *Arch. Biochem. Biophys.* 345:289-298 (1997).

Kim, et al., "Osteopontin as a Potential Diagnostic Biomarker for Ovarian Cancer," *JAMA* 287:1671-1679 (2002).

Mills, et al., "Future for Ovarian Cancer Screening: Novel Markers From Emerging Technologies of Transcriptional Profiling and Proteomics," *J. Natl. Cancer. Inst.* 93:1437-1439 (2001).

Mok, et al., "Prostasin, a Potential Serum Marker for Ovarian Cancer: Identification Through Microarray Technology," *J. Natl. Cancer Inst.* 93:1458-1464 (2001).

Peng, et al., "Proteomics: The Move to Mixtures," *J. Mass Spectrom.* 36:1083-1091 (2001).

Petricoin, et al., "Use of Proteomic Patterns in Serum to Identify Ovarian Cancer," *Lancet* 359:572-577 (2002).

Piva, et al., "Interleukin-6 Differentially Stimulates Haptoglobin Production by Peritoneal and Endometriotic Cells *in Vitro*: A Model for Endometrial-Peritoneal Interaction in Endometriosis," *J. Clin. Endocrinol. Metab.* 86:2553-2561 (2001).

Thompson, et al., "Increased Fucosylation and Other Carbohydrate Changes in Haptoglobin in Ovarian Cancer," *Cancer Letters* 66:43-48 (1992).

Vlahou, et al., "Development of a Novel Proteomic Approach for the Detection of Transitional Cell Carcinoma of the Bladder in Urine," *Am. J. Pathol.* 158:1491-1502 (2001).

Ko, et al., "Haptoglobin Typing and Quantitation in Normal Chinese Females and Gynecologic Cancer Patients," *Chinese J. Microbiol. Immunol.* 13:149-157 (1980), see especially Abstract; Database Medline, Accession No. 81089629.

Shendo, "Haptoglobin Subtyping with Anti-Haptoglobin.Alpha. Chain Antibodies," *Electrophoresis* 11:483-488 (1990), see especially Abstract; Database Caplus, Accession No. 1990:548290, (sch. Med. Akita Univ., Hondo, Japan.

Fish, et al., "Changes in Serum Acute Phase Proteins in Ovarian Cancer Patients Receiving Cis-Diamminedichloro-platinum (CDDP) Infusion Therapy," *Clinical Biochem.* 17:39-41 (1984).

* cited by examiner

DETECTION OF OVARIAN CANCER BASED UPON ALPHA-HAPTOGLOBIN LEVELS

CROSS REFERENCE TO RELATED APPLICATION

The present application claims the benefit of U.S. provisional application No. 60/296,458, filed on Jun. 8, 2001.

STATEMENT OF GOVERNMENT FUNDING

The United States Government has a paid-up license in this invention and the right in limited circumstances to require the patent owner to license others in reasonable terms as provided for by the terms of NIH Grant No. UO1CA86381 awarded by the Department of Health and Human Services.

FIELD OF THE INVENTION

The present invention is concerned with diagnostic methods that can be used in the detection of ovarian cancer. In particular, it is concerned with the detection of ovarian cancer by determining the levels of the alpha subunit of haptoglobin in women.

BACKGROUND OF THE INVENTION

The identification of novel cancer biomarkers opens the possibility for early detection, better monitoring of tumor progression, and even targeted therapy. Such markers are especially needed for ovarian cancer, which is often at an advanced stage at the time of diagnosis, leaving patients with poor prospects for survival (Mill, et al., *J. Nat'l Cancer Inst.* 93:1437–39 (2001); Daly, et al., *Cancer Cell* 1:111–2 (2002)).

Classical approaches to cancer biomarker identification involved immunizing animals with tumor cells and then screening for antibodies that recognize a cell-specific antigen (Bast, et al., *N. Engl. J. Med.* 309:883–73 (1983)). Recently, tumor mRNA has been compared with normal tissue mRNA in an attempt to identify up-regulated genes in cancer tissue using cDNA micro-arrays (Mok, et al, *J. Nat'l Cancer Inst.* 93:1458–64.3 (2001); Kim, et al., *J. Am. Med. Assoc.* 289:1671–804–5 (2002)). A limitation of the traditional approach is its high cost and labor intensity, while a limitation of the cDNA micro-array approach is that transcriptional activity in the tumor does not necessarily reflect the proteins observed peripherally.

Since protein-protein interactions and post-translational modifications (e.g. phosphorylation, glycosylation, and enzymatic cleavage) may alter the protein patterns found in a patient's circulation, proteomic high throughput approaches that allow for the identification of circulating biomarkers could accelerate oncology research. In this regard, there has been considerable interest in analyzing surface enhanced laser desorption/ionizaton mass spectrometry (SELDI-MS) spectra for markers useful for disease detection (Petricoin, et al., *Lancet* 359:572–77 (2002); Vlahou, et al., *Am. J. Pathol.* 1;158:1491–02 (2001)). If these approaches lead to a biomarker that can be used to detect ovarian cancer in its early stages, e.g., a test analogous to the Pap smear used for uterine cancer, survival rates could undoubtedly be substantially improved.

SUMMARY OF THE INVENTION

The present invention is based upon experiments in which SELDI-MS chip technology was combined with liquid chromatography and tandem mass spectrometry (LC-MS/MS), to identify a novel serum biomarker for ovarian cancer. The biomarker was identified as having an amino acid sequence corresponding to the alpha chain of haptoglobin and is consistently elevated in the serum of patients with ovarian cancer relative to the level seen in control samples from people that do not have the disease.

In its first aspect, the invention is directed to a method of assaying a woman for the presence of cancer, particularly ovarian cancer. The method involves obtaining a test biological sample, preferably a serum or plasma sample, from the woman and then assaying it to determine the amount of haptoglobin alpha chain or human haptoglobin alpha antigen present. As used herein, the terms "haptoglobin alpha chain" and "haptoglobin alpha subunit" refer to the free protein, not bound to the haptoglobin beta chain. The requirements of the protein are that it must produce an MS peak at between 11,600 and 11,700 (m/z) and have a sequence derived from human haptoglobin alpha. Peaks may be comprised of proteins that have very small differences in length due to partial degradation by protease but these differences cannot be so great as to result in an MS spectral peak outside of the specified range. Unless otherwise indicated, the terms do not refer to haptoglobin alpha chain that is part of intact haptoglobin. Similarly, the term "haptoglobin alpha antigen" refers to a protein or peptide derived from the alpha chain that has an epitope that reacts with antibody to the alpha chain and which is not bound to the beta chain or part of intact haptoglobin.

Although any means for carrying out this assay is compatible with the invention, immunological methods, particularly radioimmuno or ELISA assays, are preferred. Once a determination is made of the amount of haptoglobin alpha chain, or haptoglobin alpha antigen, present in the test sample, the results can be compared with those of control samples, which are obtained in a manner similar to the test samples but from individuals that do not have ovarian cancer. If the level of alpha haptoglobin antigen is significantly elevated in the test sample, it may be concluded that there is an increased likelihood of that the woman from which it was derived has or will develop ovarian cancer.

In an alternative embodiment, the invention is directed to a method of determining the likelihood of a woman having or developing ovarian cancer using SELDI mass spectra profiles. The procedure involves adsorbing the protein, preferably in a sample of plasma or serum, on to an immobilized metal affinity capture protein chip prior to desorption and mass spectrometry. The chip is preferably activated using $Cu^{2+}$, although other metals such as zinc or nickel may also be used. The presence of a protein peak in the spectra at between 11,600 and 11,700 (m/z) (with a 0.5% mass accuracy) is an indication that the serum sample was derived from an individual with ovarian cancer. The protein material corresponding to these peaks may be used to develop antibodies that can be used diagnostically in immunoassays.

The assays described above may be used as a screening tool or in helping to confirm a diagnosis. Thus, it is expected that the assays may be used in conjunction with clinical examinations and other tests for determining the presence of cancer. The assays may also be used in patients that have been diagnosed as having ovarian cancer to monitor the disease and the effectiveness of therapy. For example, one would expect to see a decrease in serum haptoglobin alpha chain, or antigen, levels in patients after surgery or other treatment and an increase in levels if there is a recurrence or worsening of the disease. In instances where a cancer patient is being monitored, multiple assays would be conducted over a period of months or years with the results of each new assay being compared to those from previous assays in the same patient to determine whether levels have increased or decreased. An increase in haptoglobin alpha chain would be an indication that the disease is progressing (i.e., cancer cells in the patient are growing or not adequately responding to therapy).

The invention also encompasses an antibody made by obtaining a serum or plasma sample from a patient with ovarian cancer; isolating a protein that produces a peak at between 11,600 and 11,700 (m/z) by SELDI mass spectroscopy and which has an amino sequence corresponding to a sequence of the alpha subunit of human haptoglobin; and injecting the isolated peptide into an animal capable of making said antibody. Antibodies may also be made by injecting peptides derived from the human haptoglobin alpha subunit with the peptide NNKKQWINKAVGD-KLPEC (SEQ ID NO:1) being most preferred. More generally, polyclonal or monoclonal antibodies made to these peptides by any standard method known in the art are part of the invention.

The inventors have also developed a unique ELISA assay for the human haptoglobin alpha antigen which is capable of distinguishing between the free alpha subunit and subunit that is part of intact haptoglobin. The first step in the method is to immobilize the human haptoglobin alpha antigen from a serum or plasma sample by incubating the sample on a microtiter, e.g., 96 well, plate. The antigen is then contacted with a first, preferably monoclonal, antibody that binds to intact human haptoglobin. In the next step, the plate is exposed to a second, preferably polyclonal, antibody. The second antibody binds with specificity to an epitope on the human haptoglobin alpha chain but does not bind to intact human haptoglobin after it has been bound by the first antibody. Thus, the first antibody serves to block the binding of the second to intact haptoglobin but not to free haptoglobin alpha subunit. Finally, a third antibody that is conjugated to an enzyme, e.g., horseradish peroxidase, is used for quantitating binding. The third antibody recognizes and binds to the second antibody but not to the first antibody. This may be accomplished, for example, by using a first antibody made in mouse, a second antibody made in rabbit and then a third antibody that recognizes rabbit but not mouse IgG. The reaction catalyzed by the conjugated enzyme may be then be used to quantitate binding using methods well known in the art. For example, a standard curve may be constructed using known amounts of the human haptoglobin alpha chain. A known amount of intact human haptoglobin may also be used in assays as a control.

The invention also encompasses an ELISA kit that has components needed for carrying out the assay described above. Thus, the kit contains a first antibody that binds to intact human haptoglobin and a second antibody that binds with specificity to an epitope on the human haptoglobin alpha chain but which does not bind to intact human haptoglobin that has been bound by the first antibody. Ordinarily these antibodies should be separately packaged, e.g., they should be in separate containers within the kit. The antibodies, and any other components in the kit may be lyophilized or may be in a solution optionally containing buffer, salts, stabilizing agents etc. The kit may also include components for standardizing assays and which can serves as controls. For, example the kit may include intact human haptoglobin or human haptoglobin beta chain and/or human haptoglobin alpha subunit or a peptide having at least 10 consecutive amino acids corresponding to a sequence found within that of the human haptoglobin alpha chain. These components should be in containers separate from antibody and separate from one another.

DETAILED DESCRIPTION OF THE INVENTION

The present invention is based upon the results of a study aimed at identifying potential biomarkers in the serum and plasma of women using the technique of Surface Enhanced Laser Desorption-Ionization (SELDI)-Mass Spectroscopy (MS) for the early detection of ovarian cancer. Five different types of surface specific protein chip arrays were applied to screen for potential protein markers having a molecular weight of less than 100 kDa. A total of 74 age-matched serum samples (24 cases and 50 controls) and 33 age-matched plasma samples (22 cases and 11 controls) were used. Comparing mass spectra profiles generated from the samples, several protein peaks were identified that consistently appeared in cases but not in the controls. One protein peak appeared in all subtypes of ovarian cancer cases and was further purified by affinity chromatography. Protein sequence data showed that the protein belonged to the alpha chain of haptoglobin.

Haptoglobin is a tetramer generally secreted by the liver and involved in binding free hemoglobin and preventing the loss of iron from the body. It also has peroxidase activity when it is associated with hemoglobin. The present studies have led to the concept that assays specifically directed at the alpha subunit of this protein, as opposed, for example, to the intact protein, are especially useful in the detection of ovarian cancer.

At least two types of assays may be used in the detection of ovarian cancer based upon the results described above. First, immunoassays may be used to detect the amount of haptoglobin alpha antigen in biological samples. Alternatively, mass spectroscopy may be used directly to determine whether a peak in the 11,600–11,700 (m/z) region of spectra characteristic of ovarian cancer is present. The protein material from this region may also be isolated and used in the production of antibodies that bind to it with specificity. Specificity of binding in this sense indicates an antibody that has at least a 100-fold greater affinity for an epitope on the isolated protein material than for any epitope derived from another, different, protein. The process for producing such antibodies may involve either injecting the full length protein material into an appropriate animal, or, alternatively, injecting short peptides made to correspond to different regions within a protein. The peptides should be at least five amino acids in length and should be selected from regions believed to be unique. Thus, highly conserved regions should generally be avoided in selecting peptides for the generation of antibodies. Methods for making and detecting antibodies are well known to those of skill in the art as evidenced by standard reference works such as: Harlow, et al., *Antibodies, A Laboratory Manual*, Cold Spring Harbor Laboratory, NY (1988); Klein, *Immunology: The Science of Self-Nonself Discrimination* (1982); Kennett, et al., *Monoclonal Antibodies and Hybridomas: A New Dimension in Biological Analyses* (1980); and Campbell "Monoclonal Antibody Technology," in *Laboratory Techniques in Biochemistry and Molecular Biology* (1984).

"Antibody" as used herein is meant to include intact molecules as well as fragments which retain their ability to bind to antigen (e.g., Fab and F(ab')$_2$ fragments). These fragments are typically produced by proteolytically cleaving intact antibodies using enzymes such as papain (to produce Fab fragments) or pepsin (to produce F(ab')$_2$ fragments). The term "antibody" also refers to both monoclonal antibodies and polyclonal antibodies. Polyclonal antibodies are derived from the sera of animals immunized with the antigen. Monoclonal antibodies can be prepared using hybridoma technology (Kohler, et al., *Nature* 256:495 (1975); Hammerling, et al., in *Monoclonal Antibodies and T-Cell Hybridomas*, Elsevier N.Y., pp. 563–681 (1981)). In general, this technology involves immunizing an animal, usually a mouse, with either intact antigen or a fragment derived from the antigen. The splenocytes of the immunized animals are extracted and fused with suitable myeloma cells, e.g., SP$_2$ cells. After fusion, the resulting hybridoma cells are selectively maintained in HAT medium and then cloned by limiting dilution (Wands, et al., *Gastroenterology* 80:225-232 (1981)). The cells obtained through such selection are then assayed to identify clones which secrete antibodies capable of binding specifically to antigen.

The antibodies or fragments of antibodies of the present invention may be used to detect the alpha subunits of human haptoglobin, or degradation products thereof, in radioimmunoassays or immunometric assays, also known as "two-site" or "sandwich" assays as discussed above. (See Chard, "An Introduction to Radioimmune Assay and Related Techniques," in *Laboratory Techniques in Biochemistry and Molecular Biology*, North Holland Publishing Co., NY. (1978)). In a typical immunometric assay, a quantity of unlabeled antibody is bound to a solid support that is insoluble in the fluid being tested, e.g. serum or plasma. After the initial binding of antigen to immobilized antibody, a quantity of detectably labeled second antibody (which may or may not be the same as the first) is added to permit detection and/or quantitation of bound antigen (see e.g., *Radioimmune Assay Method*, Kirkham, et al. ed., pp. 199–206, E & S Livingstone, Edinburgh (1970)). Many variations of these types of assays are know in the art and may be employed for the detection of the proteins or peptides associated with ovarian cancer.

Other types of assays for measuring the concentration of the alpha subunit of haptoglobin are also compatible with the present invention. These procedures should be distinguished from assays which measure only the intact haptoglobin protein, as it is believed that it is the alpha subunit that is particularly diagnostic of ovarian cancer, i.e., it is expected that, in general, the alpha subunits of haptoglobin will be raised in concentration to a greater extent than the beta subunits. Thus, one variation of the present invention would be to measure ratios of subunits in test patients and compare these ratios to those obtained using a control population. Control samples could be derived from the general population or, preferably, from particular individuals known to be free of ovarian cancer. Standard scientific procedures for choosing appropriate controls have been well established and may be applied in connection with the assays of the present invention.

EXAMPLES

A. Summary

The present Example describes experiments in which sera from 58 cancer patients and 50 healthy women were screened using surface enhanced laser desorption ionization (SELDI)-mass based protein chips. A candidate protein biomarker was isolated by metal affinity chromatography and sequenced by tandem mass spectrometry. An antibody was generated from a polypeptide made using the sequence data and applied for validation with Western blot and enzyme-linked immunosorbent assay (ELISA) in 80 cases, 51 benign ovarian tumors, 52 other gynecological cancers and 120 normal controls.

A protein biomarker at about 11,600 Da was identified from the serum protein profiles and showed 72% sensitivity and 90% specificity in the initial screening. The amino acid sequence showed the identity of the marker to be the alpha chain of haptoglobin (Hp-α). Western blot and ELISA data established that Hp-α was elevated up to 1.8-fold in sera of cancer patients compared to normal controls, benign tumor and other gynecological cancers (P<0.0001). This marker is especially useful for detecting early stage ovarian cancer (79% sensitivity). Complementary studies suggested that elevated Hp-α may result from cleavage of native protein rather than tumor production.

B. Materials and Methods

Biological Specimens

All patient-related biologic specimens were collected and archived under protocols approved by the Human Subjects Committees of the Partners HealthCare System, Boston, Mass. and the IRB for The University of Texas, Southwestern Medical Center at Dallas (UTSW). Serum was collected pre-operatively from women requiring surgery for a "pelvic mass," at Brigham and Women's Hospital (BWH), Massachusetts General Hospital (MGH), and UTSW. We collected serum specimens from 183 women before surgery; 80 of them proved to have epithelial ovarian cancer, 51 had benign gynecologic tumor, and 52 had other types of gynecologic cancer. A total of 120 serum specimens were also available from normal women selected from the general population and collected as part of a population-based case-control study of ovarian cancer. All specimens were aliquoted and frozen at −80° C. prior to analysis.

Serum Protein Mass Profiling

Unfractionated serum samples were thawed and mixed with an equal volume of PBS (phosphate-buffered saline) buffer (5 μl) containing 1.0% CHAPS and 8 M urea. The mixture was spun for 30-seconds before being used for protein chip binding. The protein chip IMAC3 (immobilized metal affinity capture) was activated by a metal (50 mM $Cu^{2+}$) for 10 min and followed by two washes with HPLC grade water. Serum samples were added to the surface of IMAC3 array and incubated with 40 μl binding buffer (0.1 M sodium phosphate, 0.5 M sodium chloride, 10 mM of imidazole) for 30 min. After two washes with binding buffer and water, the air-dried arrays were then treated with saturated sinapinic acid in 0.5% TFA (trifluoroacetic acid) and 50% acetonitrile before applied on SELDI-MS (Protein Biology System II, Ciphergen, Biosystems, Freemont, Calif., USA). Mass resolution and accuracy was assessed by routine calibration with 5733.58 and 12230.92 Da polypeptides. The chips were read and analyzed under the following settings: laser intensity 250, detector sensitivity 10, 50-shots per sample, auto identify peaks from 3000 to 50,000 Da. A mass accuracy of 0.1% for protein and polypeptide of 3000–30,000 mass/charge (m/z) has been obtained in this system.

Protein Purification and Identification

A serum sample of 0.5 ml from a cancer case with the pattern of interest was mixed with equal volume of PBS buffer containing 1.0% 3-[(3-cholamidopropyl) dimethylammonio]-1-propanesulfonate (CHAPS), and 8 M urea.

Then the sample was applied on a Sephadex G-25 column for desalting and removing insoluble fractions from the serum. Metal affinity column HiTrap™ chelating HP (1 ml, Amersham Pharmacia Biotech AB, Uppsala, Sweden) was applied for the metal affinity purification according to the provided protocol. Elution buffers containing 20 mM sodium phosphate, 0.5 M NaCl, pH 4.5–6.5 were applied. The eluted fractions of interest were first applied on the SELDI-MS to confirm the polypeptide peak and then separated by 10–20% gradient SDS-PAGE. The separated proteins were visualized by Coomassie staining. The band of interest was excised from the gel and subjected to in-gel digestion with trypsin (Shevchenko, et al., *Anal Chem.* 68:850–58 (1996)). The resultant polypeptides were further separated by liquid chromatography with online sequence analysis by tandem mass spectrometry (LC-MS/MS) (Peng, et al., *J. Mass Spectrom.* 36:1083–91; Mann, et al., *Annu. Rev. Biochem.* 70:437–73 (2001)). The fragmentation ladders (the b and y ion series) from the lowest mass to the highest mass were used to identify the amino acid residues of the peptides.

Antibody Generation and Western Blotting

The amino acid sequence, NNKKQWINKAVGDKLPEC (SEQ ID NO:1), from the identified Hp-α fragment was selected for peptide synthesis based on predicted antigenicity and used for generating a polyclonal antibody from rabbits (BioSource International, Hopkinton Division, Mass., USA). The affinity-purified antibody was used for the western blot and ELISA. A total of 0.5 µg of human Hp protein (98–100% purity, Sigma) was incubated with 10 µl of Hp cleavage solution (50% urea and 2% β-mercaptoethanol) (Shindo, et al., *Electrophoresis* 11:483–88 (1990)) to generate both α and β chains as positive controls. Aliquot sera (0.5 µg) samples were mixed with PBS buffer containing 1.0% CHAPS and 8 M urea before loading on the 15% SDS-PAGE. After the proteins were transferred to PVDF membrane, 5% of fat-free milk in 10 mM Tris.HCl/100 mM NaCl/0.1% (v/v) Tween-20, pH 7.5 (Tris buffer contains sodium salt and Tween-20, TBST) was used for blocking. A monoclonal antibody (1:5000) against human Hp (Sigma) was also applied for blocking the cross-reaction between Hp-α and intact Hp protein. The purified primary antibody against Hp-α was used at 1:5000 dilution in TBST with 5% milk (w/v) for 2 h. The membrane was then washed three times with TBST for 10 min per wash. The serum Hp-α peptides were detected by the second antibody conjugated to horseradish peroxidase and visualized by the enhanced chemiluminescent (ECL, Pierce) detection system.

Quantitative Validation by Enzyme-linked Immunosorbent Assay

The total Hp-α level was quantified using direct ELISA with the purified polyclonal antibody against Hp-α and the monoclonal antibody against intact Hp protein. Individual serum samples (1 µl) were mixed with 2 µl of PBS buffer containing 1.0% CHAPS and 8 M urea. The mixture was then diluted (1:1000) in coating buffer (0.1 M carbonate, pH 9.8). The diluted mixture of 200 µl was added onto a 96-well plate and incubated overnight at 4° C. for antigen coating. Antigen of the synthetic Hp-α peptide fragment was used for standard calibration in each assay. After 6 washes with buffer (5 mM Tris.HCl, 0.15M NaCl and 0.05% Tween-20), the antigen was blocked by incubation at 37° C. for 2 hours, with 1% BSA and 2–3 µg (1:5000) monoclonal antibody against human Hp protein, in the buffer containing 50 mM Tris.HCl, pH 7.5 and 0.05% NaN$_3$. After 3 washes, the polyclonal Hp-α antibody (1:3000) in 50 mM Tris.HCl, pH 7.5 with 6% BSA was added and incubated for 1 h at 37° C. After 7 washes, the second antibody conjugated with horseradish peroxidase diluted (1:5000) in 50 mM Tris.HCl, pH 7.5 with 6% BSA was applied and incubated at 37° C. for 30 min. After 9 washes, the antigen concentration was recovered by the Turbo-TMB (Pierce) initiated chemifluorescent reaction and measured at $A_{450}$ nm according to the protocol.

Real-Time Quantitative Reverse Transcription-polymerase Chain Reaction

Real-time reverse transcription-polymerase chain reaction (RT-PCR) was performed in duplicate using primer sets specific for Hp-α (forward primer: 5'CTGCGCACA-GAAGG AGATGGAGTA-3'(SEQ ID NO:2); reverse primer: 5'-GCGGACCGAGTGCTCCACATA GCC-3'(SEQ ID NO:3)). A housekeeping gene, GADPH also amplified for normalization. PCR products were detected in an ABI PRISM 5700 Sequence Detector (PE Applied Biosystems, Foster City, Calif.). RNA was extracted from normal ovarian epithelial cell cultures (HOSE 730, HOSE 854, HOSE 726) and from 8 ovarian carcinoma cell lines (MACS, OV 420, OV 2008, OVCA 429, ALST, OVCA 432, TOV 21G, RMG-1). The detailed methods for cDNA generation and PCR reaction and quantification have been previously described (Mok, et al., *J. Nat'l Cancer Inst.* 93:1458–64.3 (2001)).

Biotin Labeling Hp and Serum Enzymatic Reaction

Intact Hp protein (mixture of 1-1, 2-1 forms, Sigma) was labeled with NHS-LC-Biotin (Pierce) as previously described (Altin, et al., *Anal. Biochem.* 224:382–89 (1995)). A total of about 200 µg Hp in 200 µl PBS buffer was added with 20 times mole excess of fresh prepared NHS-LC-Biotin and incubated for 1 h at room temperature. The unlabeled free NHS-LC-Biotin was removed by micro-centrifugation. Biotin-labeled Hp (biotin-Hp, 0.4 µg) was incubated with serum samples (2 µl) at room temperature for 30 min to 6 hours. The reaction samples were applied on Western blot under non-reducing conditions. Biotin-Hp-α and -β chains were detected by enhanced chemiluminescence. The total of amount of biotin-Hp-$\alpha_1$ and biotin-Hp-$\alpha_2$ on the membrane relative to controls was quantified by densitometry and normalized with the same control sample in each blot.

Statistical Analysis

For comparison of the difference between the means of the protein marker peak intensity from SELDI-MS profiles between cancer and normal sera, Student's t test was applied on the logarithmic scale. The total Hp-α concentration in serum quantitatively measured by ELISA and biotin Hp-α, transformed to the logarithmic scale was analyzed by ANOVA to compare the difference between serum populations of ovarian cancer, benign tumor, other gynecological cancers and the normal controls.

C. Results

The SELDI-MS profile patterns of the metal binding polypeptides were displayed according to their mass-to-charge ratio (m/z) and analyzed with the biomarker software (Ciphergen) that distinguishes differences in polypeptide peaks between subject groups based on their mass intensity. One candidate marker was identifiable both by visually comparing mass spectrum profiles and by using the protein peak discriminator software. A polypeptide at approximately 11,600–11,700 Da was frequently found in cancer patients at high intensity, but less so in controls. Using 0.21 of peak intensity as a cut off (Cramer, et al., *Int. J. Cancer* 94:128–34 (2001)), this biomarker was present in 58 of the 80 cases (72%) and absent in 82 of 91 controls (90%) in the initial screening (p=0.002).

Since the profiles showing the 11,600–11,700 Da polypeptide peaks were generated from the $Cu^{2+}$ surface (IMAC3) array, this indicated that the candidate polypeptide had a metal binding affinity. Thus, a case serum was applied to a $Cu^{2+}$ activated chelating column for purification. The eluted protein fraction from the column was separated on a 10–20% gradient SDS-PAGE. The purified candidate protein from the cancer case was analyzed by SELDI-MS to confirm that it corresponded with the 11,600 Da peak. The corresponding polypeptide was unable to be purified from normal control serum.

We determined the precise amino acid sequence of the polypeptide by liquid chromatography with online sequence analysis by tandem mass spectrometry (LC-MS/MS). The sequence data showed that five different polypeptides from pro-haptoglobin-1 (Hp-1) were detected. Two of these peptides were partially tryptic peptides, which corresponded to the N and C terminus of the polypeptide biomarker. The fragmentation ladders of first polypeptide (964.5 $MH^+$, the b and y ion series) were displayed as an example for identification of the amino acid residues of PKNPANPV (SEQ ID NO:4) Q peptide. Considering all peptides detected, the amino acid sequence of the biomarker corresponded to Hp-$\alpha_1$ polypeptide.

To further explore and validate Hp-$\alpha_1$ as an ovarian cancer marker, we performed Western blot analysis using a specific polyclonal antibody against the epitope peptide to detect the Hp-$\alpha$ in serum samples. Because the peptide sequence of Hp-$\alpha_2$ is derived from gene duplication of Hp-$\alpha_1$, the polyclonal antibodies reacted with both Hp-$\alpha_1$ and Hp-$\alpha_2$, but not with $\beta$ chain as shown with Coomassie staining. Western blotting revealed that Hp-$\alpha_1$ is elevated in cancer sera but not in controls. The level of Hp-$\alpha_2$ is also increased in cancer sera. Hp $\alpha$ subunit polymorphism was also observed.

To quantify the total Hp-$\alpha$ amount in case and control sera, we developed an enzyme-linked immunosorbent assay (ELISA). A competitive monoclonal antibody against human Hp protein was used to specifically block the cross-reaction of Hp-$\alpha$ antibody with intact Hp protein. The assay, which requires 0.2 µL of serum for each, was used to screen a population of 80 patients with ovarian cancers, 51 with benign ovarian tumor, 52 with other gynecological cancers and 120 normal controls. The mean ±standard error of total Hp-$\alpha$ unit (µg/ml) in sera of ovarian cancer patients was 74.4±5.6 and significantly different (p<0.0001) from 40.7±2.1, 46±5.9 and 46±4.3 for the normal controls, benign ovarian tumor and other gynecological cancers, respectively. This preliminary assay provided the cut off value of 61 (µg/ml), which represented the mean plus one standard deviation in normal subjects, detected 67 of 80 cases (83.8%), and ruled out 99 of 120 normal controls (82.5%) as shown in Table 1. It also demonstrated that among the 19 earlier stages (I, II) cases, this marker detected 15 cases and with 79% sensitivity.

TABLE 1

Preoperative Hp-$\alpha$ level by selected subtypes with ovarian cancer and control subjects without ovarian cancer

| Characteristic | No. | Hp-$\alpha$ level, µg/ml Mean (S.D.) | Positive (>61) |
|---|---|---|---|
| Normal control | 120 | 41 (20) | 17.5% |
| Benign conditions | 51 | 46 (37) | 21.5% |
| Other GYN cancer | 52 | 46 (30) | 46% |
| Cervical carcinoma | 31 | 41 (16) | 55% |
| Endometrial carcinoma | 15 | 61.5 (30) | 20% |
| Other[1] | 6 | 87 (54) | 66% |
| Total | 223 | 47.5 (30) | 25% |

TABLE 1-continued

Preoperative Hp-$\alpha$ level by selected subtypes with ovarian cancer and control subjects without ovarian cancer

| Characteristic | No. | Hp-$\alpha$ level, µg/ml Mean (S.D.) | Positive (>61) |
|---|---|---|---|
| Ovarian cancer | | | |
| Stage I | 13 | 60.5 (22) | 69% |
| Stage II | 6 | 80.5 (34) | 100% |
| Stage III | 56 | 85.5 (53) | 86% |
| Stage IV | 5 | 76 (11) | 100% |
| Total | 80 | 74 (50) | 83.5% |

[1]Includes 1 vulva, 2 vaginal, 3 cancers of uterine body

To test whether the elevated level of Hp-$\alpha$ in the sera of ovarian cancer patients resulted from over-expression by tumor cells, quantitative RT-PCR and Western blot analysis were performed using normal and malignant ovarian epithelial cell lines. Neither the mRNA coding for Hp-$\alpha$ nor the peptide was detected. To test the hypothesis that dissociation of Hp into Hp-$\alpha$ and $\beta$ subunits may be due to the presence of specific enzymes such as proteases in the sera from cancer patients, the biotin labeled Hp (biotin-Hp) was incubated with sera from cancer patients and controls. Western blotting showed that biotin-labeled $\alpha_1$, $\alpha_2$ and $\beta$ fragments were detected in biotin-Hp samples incubated with cancer sera, and the intensity of the Hp-$\alpha_1$ increased with the time of incubation. However, only a trace of Hp-$\beta$ fragment was detected when biotin-Hp was incubated with the normal serum. With the same amount of biotin-Hp incubation, the cleaved Hp-$\alpha$ fragments were about 2-fold higher in sera from ovarian cancer patients than in sera from normal women, benign ovarian tumors, or other gynecological cancers. This is consistent with the ELISA data that total Hp-$\alpha$ is about two times higher than controls. Pretreatment of cancer sera by boiling for 10 min eliminated detectable Hp-$\alpha_1$, -$\alpha_2$, or $\beta$ subunits. This indicates that Hp-$\alpha$ dissociation from intact Hp is likely due to a specific enzymatic cleavage.

D. Discussion

Time of flight (TOF) mass spectrometry technology offers a powerful and sensitive tool for studying post-translational protein profiles in blood obtained from cancer and normal subjects. Recently, there has been considerable interest in analyzing the SELDI-MS spectral "proteomic patterns" (Petricoin, et al., *Lancet* 359:572–77 (2002). As the distinct pattern of proteins creates the discriminatory power, it may become very useful in the future for disease detection. However, validation of the methodology requires demonstration that the technique is reproducible among different laboratories and different sites of case-control specimens. Furthermore, it would be desirable to know the identity of the biomarkers in the pattern to understand their significance in disease pathogenesis. With protein identification, more standard approaches such as ELISA can then be applied for diagnostic and mechanistic studies. In fact, with mass spectrometry, a number of polypeptides have been identified that are potentially useful for diagnosis and therapy, i.e., amyloid-$\beta$ peptide as a diagnostic marker for Alzheimer's disease (Schrader, et al., *Trends Biotechnol.* 19:S55–60 (2001); Knopman, et al., *Arch. Neurol.* 58:373–379 (2001)).

Hp-$\alpha_1$ and $\alpha_2$ subunits are normally linked to the $\beta$ chain via disulfide bonds to form different Hp biotypes, which are secreted mainly from liver cells and function primarily as hemoglobin (Hb) scavengers by binding free Hb and recycling the iron. However, Hp is also recognized as an acute phase serum glycoprotein that responds to a variety of stimuli. Cells and tissues other than liver including cancer cells (Harvey, et al., *Arch. Biochem. Biophys.* 345:289–98 (1997)), intestinal, seminiferous, and endometriotic epithelium may also produce Hp (Piva, et al., *J. Clin. Endocrinol Metab.* 86:2553–61 (2001)). Besides its scavenging and inflammatory response functions, Hp has been shown to be involved in the regulation of epidermal cell transformation, immune suppression in cancer and angiogenesis. Interestingly, intact Hp has been previously found to be increased in sera from ovarian cancer patients, specifically in the glycosylated forms (Fish, et al., *Eur. J. Cancer Clin. Oncol.* 20:625–30 (1984); Thompson, et al., *Cancer Lett.* 66: 43–48 (1992)), but neither of these studies suggested any intrinsic changes in the content of Hp-α subunit.

Here we provide evidence that the Hp-α subunit is specifically elevated in sera of ovarian cancer patients. Although it is not yet clear the cause and consequence of the specific elevation of Hp-α in ovarian cancer, it is possible that the proportional dissociation of Hp-α chains from intact Hp leads to the abolition of the native Hp-Hb complex function and activation of immune suppression in cancer patients.

In conclusion, we have used MS-based protein chip technology combined with liquid chromatography and tandem mass spectrometry (LC-MS/MS) to identify Hp-α as a novel ovarian cancer serum biomarker. We have validated this biomarker by Western blot analysis and quantitative ELISA using a specific antibody. The elevated Hp-α in ovarian cancer sera is likely due to abnormal α-β cleavage in the circulation rather than tumor cell over-production. The biomarkers which resulted from the cancer-associated protein networking and metabolism, would not otherwise be detected using either the classical approach or newer ones with DNA microarrays at gene expression level. The identification of the phenotype-linked serum protein biomarkers, or the specific polypeptide markers using proteomic approaches should profoundly affect cancer diagnosis and broaden our understanding of molecular mechanisms in cancer biology.

All references cited herein are fully incorporated by reference. Having now fully described the invention, it will be understood by those of skill in the art that the invention may be performed within a wide and equivalent range of conditions, parameters and the like, without affecting the spirit or scope of the invention or any embodiment thereof.

What is claimed is:

1. A method of assaying a woman for ovarian cancer, comprising:
   a) obtaining a test sample of serum, plasma, or whole blood from said woman;
   b) assaying said test sample to determine the amount of free human haptoglobin alpha subunit that is present;
   c) comparing the amount of free human haptoglobin alpha subunit determined in step b) with the amount of free human haptoglobin alpha subunit in a control sample of serum, plasma or whole blood; and
   d) determining if said woman is at increased risk of having ovarian cancer based upon the comparison of step c).

2. The method of claim 1, wherein the amount of free human haptoglobin alpha subunit present in said test sample is determined using an immunoassay.

3. The method of claim 2, wherein said immunoassay is a radioimmunoassay.

4. The method of claim 2, wherein said immunoassay is an ELISA.

5. The method of any one of claims 2–4, wherein said immunoassay, radioimmunoassay or ELISA is performed using an antibody that only recognizes the free human haptoglobin alpha subunit and which does not recognize this subunit when joined to the haptoglobin beta chain.

6. The method of claim 5, wherein said antibody is a monoclonal antibody.

7. The method of any one of claims 1–4, wherein said test sample is serum.

8. The method of any one of claims 1–4, wherein said test sample is plasma.

9. The method of any one of claims 1–4, wherein said test sample is whole blood.

10. A method of assaying a woman for the effectiveness of ovarian cancer therapy, comprising:
    a) obtaining a test sample of serum, plasma, or whole blood from said woman;
    b) assaying said test sample to determine the amount of free human haptoglobin alpha subunit that is present;
    c) comparing the amount of free human haptoglobin alpha subunit determined in step b) with the amount of free human haptoglobin alpha subunit determined in an assay previously performed on a sample of serum, oplasma or wholeblood from said woman of serum, plasma or whole blood; and
    d) determining if said woman is at increased risk of having ovarian cancer based upon the comparison of step c).

11. The method of claim 10, wherein the amount of free human haptoglobin alpha subunit present in said test sample is determined using an immunoassay.

12. The method of claim 11, wherein said immunoassay is a radioimmunoassay.

13. The method of claim 12, wherein said immunoassay is an ELISA.

14. The method of any one of claims 11–13, wherein said immunoassay, radioimmunoassay or ELISA is performed using an antibody that only recognizes free human haptoglobin alpha subunit and which does not recognize this subunit when joined to the human haptoglobin beta chain.

15. The method of claim 14, wherein said antibody is a monoclonal antibody.

16. The method of any one of claim 10–13, wherein said test sample is serum.

17. The method of any one of claims 10–13, wherein said test sample is plasma.

18. The method of any one of claims 10–13, wherein said test sample is whole blood.

* * * * *

SEQUENCE LISTING

<160> NUMBER OF SEQ ID NOS: 4

<210> SEQ ID NO 1
<211> LENGTH: 18
<212> TYPE: PRT
<213> ORGANISM: Homo sapiens

<400> SEQUENCE: 1

Asn Asn Lys Lys Gln Trp Ile Asn Lys Ala Val Gly Asp Lys Leu Pro
1               5                   10                  15

Glu Cys

<210> SEQ ID NO 2
<211> LENGTH: 24
<212> TYPE: DNA
<213> ORGANISM: Homo sapiens

<400> SEQUENCE: 2
ctgcgcacag aaggagatgg agta                                          24

<210> SEQ ID NO 3
<211> LENGTH: 24
<212> TYPE: DNA
<213> ORGANISM: Homo sapiens

<400> SEQUENCE: 3
gcggaccgag tgctccacat agcc                                          24

<210> SEQ ID NO 4
<211> LENGTH: 8
<212> TYPE: PRT
<213> ORGANISM: Homo sapiens

<400> SEQUENCE: 4

Pro Lys Asn Pro Ala Asn Pro Val
1               5